(12) United States Patent
Sabahi et al.

(10) Patent No.: US 8,766,016 B2
(45) Date of Patent: Jul. 1, 2014

(54) GREEN AND ATOM-ECONOMICAL PROCESSES FOR PRODUCING PHENOLIC ANTIOXIDANTS

(75) Inventors: Mahmood Sabahi, Baton Rouge, LA (US); Thomas Robert Nicholas, Orangeburg, SC (US)

(73) Assignee: Albermarle Corporation, Baton Rouge, LA (US)

( * ) Notice: Subject to any disclaimer, the term of this patent is extended or adjusted under 35 U.S.C. 154(b) by 138 days.

(21) Appl. No.: 13/382,683

(22) PCT Filed: Jul. 6, 2010

(86) PCT No.: PCT/US2010/041029
§ 371 (c)(1),
(2), (4) Date: Jan. 6, 2012

(87) PCT Pub. No.: WO2011/005735
PCT Pub. Date: Jan. 13, 2011

(65) Prior Publication Data
US 2012/0108854 A1 May 3, 2012

Related U.S. Application Data

(60) Provisional application No. 61/224,717, filed on Jul. 10, 2009.

(51) Int. Cl.
*C07C 39/06* (2006.01)

(52) U.S. Cl.
USPC ............................................ 568/727; 568/720

(58) Field of Classification Search
USPC .................................................. 568/720, 727
See application file for complete search history.

(56) References Cited

U.S. PATENT DOCUMENTS

| 3,925,488 A | 12/1975 | Shin |
| 4,754,077 A | 6/1988 | Mina |
| 5,292,969 A * | 3/1994 | Berris ........................ 568/720 |

FOREIGN PATENT DOCUMENTS

| EP | 0 065 289 A1 | 11/1982 |
| EP | 0 420 025 A2 | 4/1991 |
| GB | 1 202 762 A | 8/1970 |
| JP | 61030544 A | 2/1986 |
| WO | 8402336 A1 | 6/1984 |

* cited by examiner

*Primary Examiner* — Sudhakar Katakam
*Assistant Examiner* — Pancham Bakshi
(74) *Attorney, Agent, or Firm* — James A. Jubinsky; Marcy M. Hoefling; Nathan C. Dunn

(57) ABSTRACT

Processes for producing 1,3,5-trimethyl-2,4,6-tris(3,5-di-alkyl-4-hydroxybenzyl)benzene are provided, in particular such processes that utilize 2,6-di-tert-butylphenol, paraformaldehyde, a secondary amine, mesitylene, and acetic acid.

18 Claims, No Drawings

GREEN AND ATOM-ECONOMICAL PROCESSES FOR PRODUCING PHENOLIC ANTIOXIDANTS

BACKGROUND

When added to fuels, and/or used in the production thereof, phenolic antioxidants can extend storage life and protect fuel systems, increase resistance to oxidation, help control insoluble gum formation, and help petroleum and biofuel refiners and marketers meet stringent government regulations and OEM standards, including those requiring reduced emissions.

When added to lubricants, and/or used in the production thereof, phenolic antioxidants can enhance thermal stability, improve lubricant performance and reduce sludge formation, extending the useful life of lubricants in virtually any application. They reduce thickening and inhibit acid formation in a variety of applications, including engine oils, automatic transmission fluids, industrial oils, as well as compressor oil and gear and hydraulic oils.

When added to polymers, and/or used in the production thereof, phenolic antioxidants can maintain the performance integrity and processing stability of plastics, elastomers, adhesives and other materials.

It is known that 1,3,5-trimethyl-2,4,6-tris(3,5-dialkyl-4-hydroxybenzyl)benzenes are useful phenolic antioxidants—and processes for making these 1,3,5-trimethyl-2,4,6-tris(3,5-dialkyl-4-hydroxybenzyl)benzenes are known. For example, it is known that 1,3,5-trimethyl-2,4,6-tris(3,5-dialkyl-4-hydroxybenzyl)benzenes can be prepared by reacting mesitylene with the appropriate 2,6-dialkyl-4-methoxymethylphenol in the presence of an acidic catalyst. See, e.g., U.S. Pat. Nos. 4,992,597 (Mina et al.), 4,994,628 (Goddard et al.), and 5,292,969 (Berris). See also International Publication No. WO 84/02336 (Mina).

However, given the extensive need for all of the products in which 1,3,5-trimethyl-2,4,6-tris(3,5-dialkyl-4-hydroxybenzyl)benzene antioxidants are useful, there is a need for improved and environmentally friendly "green" processes for producing such antioxidants that would eliminate the use of hazardous solvents, eliminate the isolation of intermediates, significantly reduce hazardous waste, and lower costs.

THE INVENTION

This invention meets the above-described needs by providing processes for producing 1,3,5-trimethyl-2,4,6-tris(3,5-dialkyl-4-hydroxybenzyl)benzene ("Product"), which processes comprise combining at least acetic acid, paraformaldehyde, 2,6-di-tert-butylphenol, and a secondary amine to yield at least 2,6-di-tert-butyl-4-acetoxymethylphenol, isolating at least the 2,6-di-tert-butyl-4-acetoxymethylphenol as a solid or a melt, dissolving at least the 2,6-di-tert-butyl-4-acetoxymethylphenol in acetic acid to form a solution, combining at least the solution, mesitylene, and a catalytic amount of an acid catalyst, and yielding at least a 1,3,5-trimethyl-2,4,6-tris(3,5-dialkyl-4-hydroxybenzyl)benzene. Such processes further comprise recovering the acetic acid for use in another process.

This invention also provides processes for producing 1,3,5-trimethyl-2,4,6-tris(3,5-dialkyl-4-hydroxybenzyl)benzene, which processes comprise combining acetic acid, paraformaldehyde, a secondary amine, and 2,6-di-tert-butylphenol to yield a solution comprising at least 2,6-di-tert-butyl-4-acetoxymethylphenol, combining at least the solution, mesitylene, and a catalytic amount of an acid catalyst, and yielding at least a 1,3,5-trimethyl-2,4,6-tris(3,5-dialkyl-4-hydroxybenzyl)benzene. In such processes, 2,6-di-tert-butyl-4-acetoxymethylphenol is produced in situ, and no isolation step is required. Also provided are processes that comprise combining at least acetic acid, paraformaldehyde, a secondary amine, and 2,6-di-tert-butylphenol to yield at least 2,6-di-tert-butyl-4-acetoxymethylphenol, combining at least the 2,6-di-tert-butyl-4-acetoxymethylphenol, mesitylene, and a catalytic amount of an acid catalyst, and yielding at least 1,3,5-trimethyl-2,4,6-tris(3,5-dialkyl-4-hydroxybenzyl)benzene. Also provided are such processes wherein the paraformaldehyde is in excess as to the 2,6-di-tert-butylphenol, and wherein unreacted paraformaldehyde is recovered.

This invention also provides product compositions comprising 2,6-di-tert-butyl-4-acetoxymethylphenol, 2,6-di-tert-butylphenol, 2,6-di-tert-butyl-4-hydroxymethylphenol, and 4,4'-methylenebis(2,6-di-tert-butylphenol).

Also provided are processes that comprise combining at least acetic acid, paraformaldehyde, a secondary amine, and 2,6-di-tert-butylphenol to yield at least 2,6-di-tert-butyl-4-acetoxymethylphenol, isolating at least the 2,6-di-tert-butyl-4-acetoxymethylphenol as a solid or a melt, dissolving at least the 2,6-di-tert-butyl-4-acetoxymethylphenol solid or melt in at least acetic acid to form a solution, combining at least the solution, mesitylene, and a catalytic amount of an acid catalyst, and yielding at least a 1,3,5-trimethyl-2,4,6-tris(3,5-dialkyl-4-hydroxybenzyl)benzene.

Also provided are processes that comprise combining at least acetic acid, paraformaldehyde, a secondary amine, and 2,6-di-tert-butylphenol to yield at least 2,6-di-tert-butyl-4-acetoxymethylphenol, isolating at least the 2,6-di-tert-butyl-4-acetoxymethylphenol as a solid or a melt, combining at least the 2,6-di-tert-butyl-4-acetoxymethylphenol, mesitylene, and a catalytic amount of an acid catalyst, and yielding at least a 1,3,5-trimethyl-2,4,6-tris(3,5-dialkyl-4-hydroxybenzyl)benzene.

Also provided are processes that comprise combining at least acetic acid, paraformaldehyde, a secondary amine, and 2,6-di-Cert-butylphenol to yield a solution comprising at least 2,6-di-tert-butyl-4-acetoxymethylphenol, acidifying the solution, combining at least the 2,6-di-tert-butyl-4-acetoxymethylphenol, mesitylene, and a catalytic amount of an acid catalyst, and yielding at least a 1,3,5-trimethyl-2,4,6-tris(3,5-dialkyl-4-hydroxybenzyl)benzene.

Also provided are processes that comprise combining at least 2,6-di-tert-butyl-4-methoxymethylphenol, acetic acid, mesitylene, and an acid catalyst, and yielding at least 1,3,5-trimethyl-2,4,6-tris(3,5-dialkyl-4-hydroxybenzyl)benzene.

The reaction scheme for one of the processes of this invention can be illustrated as follows:

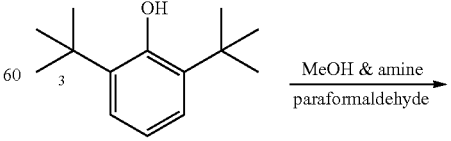

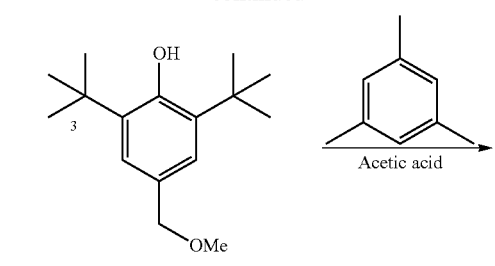

2,6-di-t-butyl-4-methoxymethylphenol

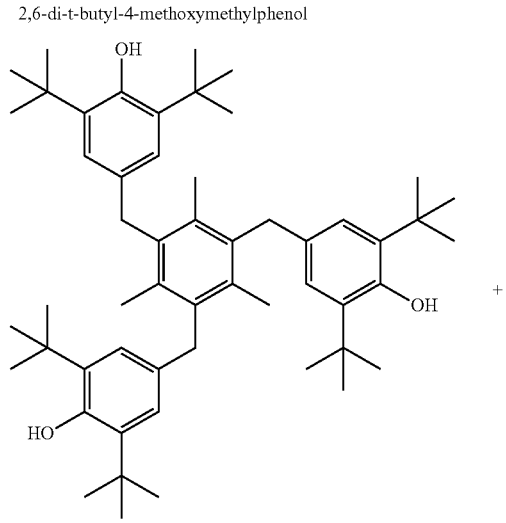

3 MeOH

In this process, 2,6-di-tert-butyl-4-methoxymethylphenol is dissolved in acetic acid and reacted with mesitylene in the presence of an acid catalyst like sulfuric acid to produce at least 1,3,5-trimethyl-2,4,6-tris(3,5-dialkyl-4-hydroxybenzyl)benzene. Alternatively, 2,6-di-tert-butyl-4-methoxymethylphenol may be dissolved in acetic acid and converted to 2,6-di-t-butyl-4-acetoxymethylphenol in the presence of catalytic amount of an acid catalyst and at temperatures of 20 to 100° C. followed by the addition of mesitylene to produce at least 1,3,5-trimethyl-2,4,6-tris(3,5-dialkyl-4-hydroxybenzyl)benzene.

The reaction scheme for another one of the processes of this invention can be illustrated as follows:

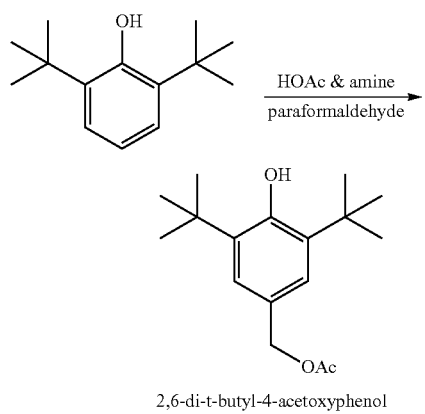

2,6-di-t-butyl-4-acetoxyphenol

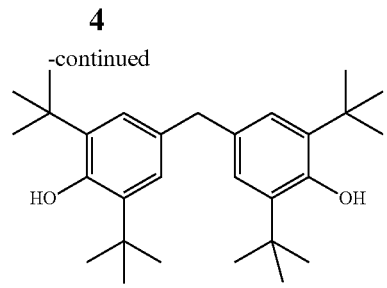

In this process, the intermediate 2,6-di-t-butyl-4-acetoxymethylphenol is prepared from the reaction of 2,6-di-t-butylphenol with paraformaldehyde in acetic acid solvent and a secondary amine producing a composition comprising 2,6-di-tert-butyl-4-acetoxymethylphenol, 2,6-di-tert-butylphenol, 2,6-di-tert-butyl-4-hydroxymethylphenol, and 4,4'-methylenebis(2,6-di-tert-butylphenol). The product 2,6-di-t-butyl-4-acetoxymethylphenol may be purified by crystallization or precipitation from the reaction mass. Or the reaction mass maybe used for reaction with mesitylene in the presence of and acid catalyst. Paraformaldehyde and 2,6-di-t-butylphenol may be used in equal molar amounts or a 10 to 50% molar excess of formaldehyde may be used in producing the compositions of this invention.

The reaction scheme for another one of the processes of this invention can be illustrated as follows:

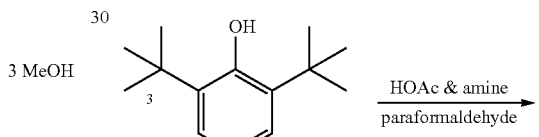

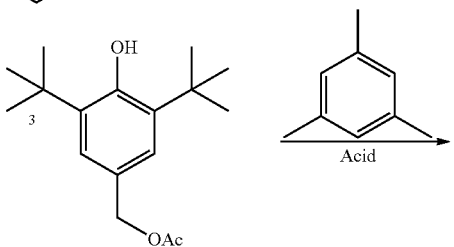

2,6-di-t-butyl-4-acetoxymethylphenol

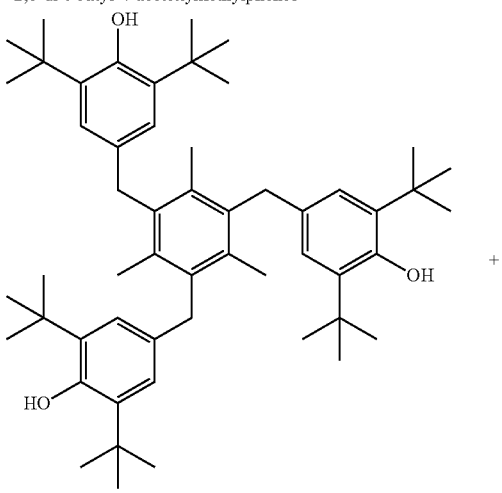

3 Acetic acid

In this process, the intermediate 2,6-di-t-butyl-4-acetoxymethylphenol is prepared from the reaction of 2,6-di-t-butylphenol with excess paraformaldehyde in acetic acid solvent and a secondary amine. The intermediate 2,6-di-t-butyl-4-acetoxymethylphenol may be purified in the molten state by repeated washing with water to remove excess formaldehyde. It may further be purified by crystallization from acetic acid. Alternatively, it may be precipitated from a hydrocarbon solvent like heptane and filtered. Or, it may be crystallized from the reaction mixture by cooling the acetic acid reaction mixture to 0-15° C., and subsequently filtering the solid product. The product may be further purified by re-crystallization.

Yet another reaction scheme for the processes of this invention can be illustrated as follows:

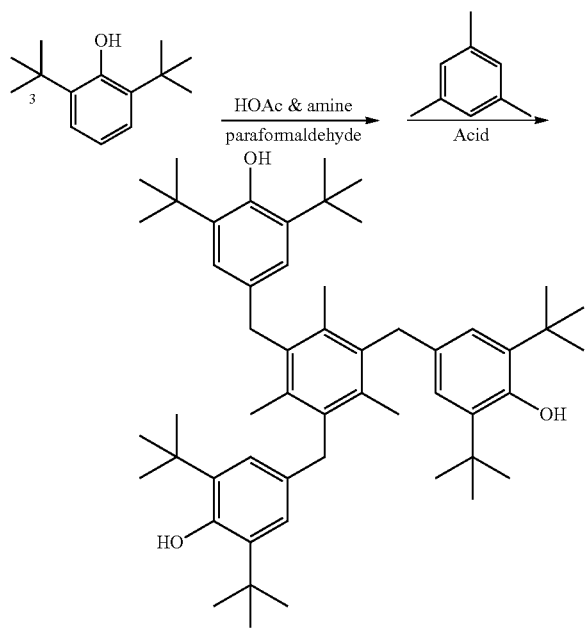

In this one-pot, two-step, one solvent process, 2,6-di-tert-butylphenol is first reacted with paraformaldehyde in acetic acid in the presence of a secondary amine followed by the acidification of the reaction mixture with an acid and addition of mesitylene producing 1,3,5-trimethyl-2,4,6-tris(3,5-dialkyl-4-hydroxybenzyl)benzene which is precipitated on cooling the reaction mixture to 5-10° C. and isolating the product by filtration.

In the processes of this invention, 2,6-di-tert-butylphenol maybe used as a solid, or dissolved in the appropriate solvent, or as a melt. In the laboratory operations, it was usually dissolved in the solvent of the reaction for convenience. However, it is known to the people skilled in the art that in industrial operations it would conveniently be utilized as a melt (liquid) with or without the use of a diluting solvent.

This invention is advantageous in that Product can be produced in the absence of a hydrocarbon solvent or a halohydrocarbon solvent, such as dichloromethane or 1,1,1-trichloroethane, or an alcohol such as methanol. Moreover, the process is carried out with an environmentally friendly "green" solvent like acetic acid which can be recycled thus minimizing emissions and hazardous waste. This process also eliminates isolation and purification of intermediates and reduces aqueous waste and organic wastes. This invention is additionally advantageous in that the intermediate 2,6-dialkyl-4-acetoxymethylphenol can be produced in situ from 2,6-di-tert-butylphenol or 2,6-dialkyl-4-methoxymethylphenol and used without isolation or purification to produce 1,3,5-trimethyl-2,4,6-tris(3,5-di-tert-butyl-4-hydroxybenzyl)benzene.

The 2,6-diallylphenol moiety of the 2,6-dialkyl-4-methoxymethylphenol and 2,6-dialkyl-4-acetoxymethylphenol which are reacted with mesitylene in the practice of this invention may be any one or more of the 2,6-dialkylphenol moieties of the 2,6-dialkyl-4-methoxymethylphenols of Mina et al. and Goddard et al., the teachings of which are incorporated herein by reference. Thus, as in Mina et al. and Goddard et al., the "alkyl" groups in the 2- and 6-positions may be alkyl, cycloalkyl, or aralkyl groups and may be the same or different; and the phenols include, e.g., the 2,6-dimethyl-, 2,6-diisopropyl-, 2,6-diisobutyl-, 2,6-di-sec-butyl-, 2,6-di-t-butyl-, 2,6-dicyclopentyl-, 2,6-dicyclohexyl-, 2,6-dibenzyl-, 2,6-di(α-methylbenzyl)-, 2-methyl-6-t-butyl-, 2-methyl-6-t-octyl-, 2-methyl-6-cyclopentyl-, 2-methyl-6-benzyl-, 2-methyl-6-(α-methylbenzyl)-, 2-isopropyl-6-(α,α-dimethylbenzyl)-, and 2-t-butyl-6-cyclooctyl-4-phenols.

As is customary in 1,3,5-trimethyl-2,4,6-tris(3,5-dialkyl-4-hydroxybenzyl)benzene syntheses, the 2,6-dialkyl-4-methoxymethylphenol and 2,6-dialkyl-4-acetoxymethylphenol are employed in a stoichiometric sufficiency or excess, usually an amount such as to provide about 3-5, or about 3.3-4.0 mols of the phenol per mol of mesitylene.

Processes of this invention utilize carboxylic acids with boiling points that are low, i.e., about the same as carboxylic acids such as acetic acid, propionic acid, and butyric acid, all of which can be used in processes of this invention.

Processes of this invention utilize acid catalysts that are Bronsted acids and organic acids that have acidities stronger than acetic or propionic acid. Such acid catalysts have acidities stronger than carboxylic acids like acetic acid. Examples of such acids are alkyl sulfonic acids, aryl sulfonic acids, chloroacetic acid, trifluoroacetic acid, sulfuric acid and the like.

Processes of this invention utilize secondary amines like dimethylamine, diethylamine, methylethyl amine, diisopropylamine, methylisoproplyamine, ethylisopropylamine, dipropylamine, methylproplyamine, ethylpropylamine, di-butylamine, methylbutylamine, ethylbutylamine, proplybutylamine, diphenylamine, phenylnaphthylamine, piperidine, piperazine and the like. The secondary amine acts as a catalyst in reactions that occur in processes of this invention.

Processes of this invention can be conducted from about 50° C. to about 120° C. with catalytic amounts of acid.

In the processes of this invention, the Product having 97-99.5% purity can be precipitated out of the reaction mixture as soon as it is formed. At the end of the reaction, the Product can simply be filtered in air; the solid Product can be washed with water to remove acetic acid and dried at about 100° C. under reduced pressure. Product may be further purified by re-crystallization from an appropriate solvent.

EXAMPLES

The following examples are illustrative of the principles of this invention. It is understood that this invention is not limited to any one specific embodiment exemplified herein, whether in the examples or the remainder of this patent application.

Example 1

Preparation of 1,3,5-trimethyl-2,4,6-tris(3,5-di-tert-butyl-4-hydroxybenzyl)benzene In a four-necked flask equipped with a stirrer, distillation head, heated-addition funnel, and thermometer was placed mesitylene (30 g, 0.25 mol) and acetic acid (52 g) at room temperature and under a mild flow of nitrogen. 2,6-di-tert-Butyl-4-methoxymethylphenol (213.5 g of 89.2 wt %, 0.76 mol) was dissolved in acetic acid (520 g) and placed in the heated addition funnel (total volume of 750 mL) and a fraction of it (27%) was added to the reaction mixture and heated to 70° C. Sulfuric acid (3.9 g of 98%) was added with stirring and after five minutes, the addition of 2,6-di-tert-butyl-4-methoxymethylphenol solution at 70° C. was started and it was completed in three hours. The condensate was collected and analysis showed a mixture of methyl acetate and acetic acid. After a total of six hours at 70° C., acetic acid was partially removed by distillation under reduced pressure (225 g, at 50-55° C. and 70 mmHg). The resulting slurry was filtered and the solid was dried in air (196.3 g) then dissolved in heptane (1000 g) and heated to 75-80° C. and washed with water (2×500 g) and adjusted the pH to about 5 by addition of potassium carbonate. The organic phase was dried by azeotropic distillation. Upon cooling to about 5° C., 1,3,5-trimethyl-2,4,6-tris(3,5-di-tert-butyl-4-hydroxybenzyl)benzene precipitated as a white powder that was isolated and dried. LC analysis showed 98.5% of 1,3,5-trimethyl-2,4,6-tris(3,5-di-tert-butyl-4-hydroxybenzyl)benzene, and 0.21 wt % of 1,3,5-trimethyl-2,4-di(3,5-di-tert-butyl-4-hydroxybenzyl)benzene.

Example 2

Preparation of 1,3,5-trimethyl-2,4,6-tris(3,5-di-tert-butyl-4-hydroxybenzyl)benzene Example 1 was repeated but 2,6-di-tert-butyl-4-methoxymethylphenol (213.5 g of 89.2 wt %, 0.76 mol) was added as a melt to the reaction mixture.

Example 3

Preparation of 1,3,5-trimethyl-2,4,6-tris(3,5-di-tert-butyl-4-hydroxybenzyl)benzene Mesitylene (12 g, 0.1 mol) and 2,6-di-tert-butyl-4-methoxymethylphenol (80 g of 98%, 0.31 mol) were added to a reactor containing acetic acid (280 g) and the mixture was stirred at room temperature under nitrogen. Sulfuric acid (0.5 g of 98%) was added and the reaction mixture was heated at 60° C. for six hours. The resulting slurry was filtered and the solid was washed with water (500 g), dissolved in heptane and dried by azeotropic removal of water. The product, 1,3,5-trimethyl-2,4,6-tris(3,5-di-tert-butyl-4-hydroxybenzyl)benzene, precipitated on cooling to 0-5° C. and isolated as white powder (63 g, 81.4%). Analysis showed 97.4% of 1,3,5-trimethyl-2,4,6-tris(3,5-di-tert-butyl-4-hydroxybenzyl)benzene, and 1.9 wt % of 1,3,5-trimethyl-2,4-di(3,5-di-tert-butyl-4-hydroxybenzyl)benzene.

Example 4

Preparation of 1,3,5-trimethyl-2,4,6-tris(3,5-di-tert-butyl-4-hydroxybenzyl)benzene from 2,6-di-tert-butyl-4-acetoxymethylphenol Example 4(a)

Preparation of 2,6-di-tert-butyl-4-acetoxymethylphenol 2,6-di-tert-Butylphenol (131.8 g, 0.64 mol) was dissolved in acetic acid (150 g) and the resulting solution was added to a flask containing paraformaldehyde (26.2 g of 95%), diethyl amine (5.8 g) and acetic acid (450 g) over a period of five hours and at reflux temperature. After 11 hrs, most of the solvent was removed under reduced pressure and 65° C. and the residue was heated to 85-90° C. and the resulting melt was washed with hot water at 90-95° C. (3×200 g). The product was dried by addition of heptane and azeotropic distillation and isolated as a bright yellow solid (178 g) after cooling to about 5° C. Analysis by GC-mass, GC, and NMR showed a product comprising 2,6-di-tert-butyl-4-acetoxymethylphenol (85.5%), 2,6-di-tert-butylphenol (0.6%), 2,6-di-tort-butyl-4-hydroxymethylphenol (2.5%), and 4,4'-methylenebis (2,6-di-test-butylphenol) (4%).

Example 4(b)

Preparation of 1,3,5-trimethyl-2,4,6-tris(3,5-di-tert-butyl-4-hydroxybenzyl)benzene To an acetic acid solution of 73 g of the thus produced product comprising 2,6-di-tert-butyl-4-acetoxymethylphenol (85.5% by GC) was added mesitylene (2.4 g) and sulfuric acid (2 g, 98%); the resulting solution was heated at 60° C. for six hours. Most of the acetic acid was removed under reduced pressure and 65-70° C.; the resulting paste was dissolved in heptane (120 g); and the resulting solution was washed with water (2×60 g) at 70-75° C. The solution was dried by azeotropic removal of water and cooled to ambient temperature; 1,3,5-trimethyl-2,4,6-tris(3,5-di-tert-butyl-4-hydroxybenzyl)benzene was isolated as an off-white solid (8.1 g).

Example 4(c)

Preparation of 1,3,5-trimethyl-2,4,6-tris(3,5-di-tert-butyl-4-hydroxybenzyl)benzene Experiment 3(b) was repeated with the crude acetic acid solution of 2,6-di-tert-butyl-4-acetoxymethylphenol (170 g), mesitylene (18.6 g), and sulfuric acid (5 g). After three hours of heating at 60° C. the reaction mixture was poured over cold water (500 g) and the solid precipitate was filtered and dried in air. The crude product was dissolved in heptane (600 g), washed the organic layer with water (3×100 g) at 80° C., and dried by azeotropic distillation. Product was precipitated after cooling to 2-3° C. and isolated as an off-white solid (75 g). Analysis showed 97.1% of 1,3,5-trimethyl-2,4,6-tris(3,5-di-tert-butyl-4-hydroxybenzyl)benzene and 1.9 wt % 1,3,5-trimethyl-2,4-di(3,5-di-tert-butyl-4-hydroxybenzyl)benzene.

Example 4(d)

Preparation of 1,3,5-trimethyl-2,4,6-tris(3,5-di-tert-butyl-4-hydroxybenzyl)benzene A portion of the produced product was processed to provide a product of improved purity, comprising 2,6-di-tert-butyl-4-acetoxymethylphenol (95%). A three-necked flask was charged with the thus-produced 2,6-di-tort-butyl-4-acetoxymethylphenol (18.1 g of 95%), mesitylene (2.4 g), acetic acid (80 g), and sulfuric acid (1 g, 98%) at room temperature and under nitrogen. The reaction mixture was stirred at room temperature for 22 hrs and at 60° C. for five more hours. The slurry was cooled to 10° C. and filtered and the solid was washed with water (400 mL) and dried under vacuum at 70-75° C. to afford 13.8 g white powder. LC— Analysis showed 99% 1,3,5-trimethyl-2,4,6-tris(3,5-di-tert-butyl-4-hydroxybenzyl)benzene, 0.7 wt % 1,3,5-trimethyl-2,4-di(3, 5-di-tert-butyl-4-hydroxybenzyl)benzene, and 0.02 wt % of 4,4'-methylenebis(2,6-di-tert-butylphenol).

Example 5

Preparation of 1,3,5-trimethyl-2,4,6-tris(3,5-di-tert-butyl-4-hydroxybenzyl)benzene from 2,6-di-tert-butylphenol In a four-necked flask equipped with a stirrer, condenser, thermocouple, and an addition funned was placed paraformaldehyde (26.2 g of 95%), diethyl amine (6.2 g), and acetic acid (350). 2,6-di-tert-Butylphenol (132 g) was dissolved in acetic acid (150 g) and placed in the addition funnel. A portion of this solution (38%) was added to the stirred reaction mixture at room temperature and heated up to 110° C. After one hour another portion (31%) was added and refluxing was continued. After two hours at these conditions, the rest of the solution (31%) was added and refluxed for a total of eight hours. The reaction mixture was concentrated under reduced pressure and at 65° C. and the resulting paste was washed with water (3×150 g) at 95-100° C. Heptane (200 g) was added to the residue and dried by azeotropic distillation. Heptane was removed under vacuum at 70° C. Crude product weighed 154 g with a purity of 83% by GC. This was re-dissolved in acetic acid (460 g) and mesitylene (18 g) was added and stirred at room temperature. Sulfuric acid (5 g, 98%) was added and heated at 40° C. for five hours. GC Analysis showed less than 2% unreacted starting material. The reaction slurry was added to water (700 g) and filtered. The crude solid was dissolved in heptane (500 g) and heated to 85° C. and the organic layer was washed with water (3×100 g) and dried by azeotropic distillation. The solvent was removed under reduced pressure and 1,3,5-trimethyl-2,4,6-tris(3,5-di-tert-butyl-4-hydroxybenzyl)benzene was isolated as an off-white powder (95 g).

Example 6

Preparation of 1,3,5-trimethyl-2,4,6-tris(3,5-di-tert-butyl-4-hydroxybenzyl)benzene from 2,6-di-tert-butylphenol In a four-necked flask equipped with a stirrer, condenser, thermocouple, and an addition funned was placed paraformaldehyde (20.5 g of 95%), diethyl amine (4.3 g), and acetic acid (250). 2,6-di-tert-Butylphenol (112 g) was dissolved in acetic acid (200 g) and placed in the addition funnel. A portion of this solution (67%) was added to the stirred reaction mixture at room temperature and heated up to 110° C. After three hours the rest of solution was added and refluxing was continued for a total of six hours. NMR assay showed a 23 wt % solution of 2,6-di-tert-butyl-4-acetoxymethylphenol. Mesitylene (17.2 g) was added, the mixture was stirred, sulfuric acid (14 g, 98%) was added, and the mixture was heated and held at 50° C. for five hours. GC Analysis showed the presence of unreacted starting material. The reaction mixture was heated and held at 80° C. for one hour. The reaction slurry was cooled to 5° C. and filtered. The resulting pink powder was heated under vacuum (10-15 mmHg) and 75° C. for one hour. Analysis of the product (86 g) showed 96.1% of 1,3,5-trimethyl-2,4,6-tris(3,5-di-tert-butyl-4-hydroxybenzyl)benzene and 1.9 wt % of 1,3,5-trimethyl-2,4-di(3,5-di-tert-butyl-4-hydroxybenzyl)benzene. Analysis of the filtrate showed 2.22 wt % 1,3,5-trimethyl-2,4-di(3,5-di-tert-butyl-4-hydroxybenzyl)benzene and 0.4 wt % of 1,3,5-trimethyl-2,4,6-tris(3,5-di-tert-butyl-4-hydroxybenzyl)benzene along with other impurities.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, in situ blended or mixed with one or more other substances, components and/or ingredients in accordance with the present disclosure. Whatever transformations, if any, which occur as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

The invention claimed is:

1. A process comprising:
combining in a container at least acetic acid, paraformaldehyde, a secondary amine, and 2,6-di-tert-butylphenol and refluxing at about 100° C. to about 140° C. for at least about 2 hours,
adding mesitylene and a catalytic amount of an acid catalyst to the container, and yielding at least 1,3,5-trimethyl-2,4,6-tris(3,5-di-tert-butyl-4-hydroxybenzyl)benzene having a purity of at least about 98%, wherein said process is produced in the absence of a hydrocarbon solvent or a halohydrocarbon solvent.

2. A process comprising:
combining at least acetic acid, paraformaldehyde, a secondary amine, and 2,6-di-tert-butylphenol to yield a solution comprising at least 2,6-di-tert-butyl-4-acetoxymethylphenol,
combining at least the solution, mesitylene, and a catalytic amount of an acid catalyst, and
yielding at least 1,3,5-trimethyl-2,4,6-tris(3,5-di-tert-butyl-4-hydroxybenzyl)benzene, wherein said process is produced in the absence of a hydrocarbon solvent or a halohydrocarbon solvent.

3. The process according to claim 2 wherein the paraformaldehyde is in excess as to the 2,6-di-tert-butylphenol.

4. The process according to claim 3 further comprising recovering unreacted paraformaldehyde.

5. A process comprising:
combining at least acetic acid, paraformaldehyde, a secondary amine, and 2,6-di-tert-butylphenol to yield at least 2,6-di-tert-butyl-4-acetoxymethylphenol,
isolating at least the 2,6-di-tert-butyl-4-acetoxymethylphenol as a solid or a melt,
dissolving at least the 2,6-di-tert-butyl-4-acetoxymethylphenol solid or melt in at least acetic acid to form a solution,
combining at least the solution, mesitylene, and a catalytic amount of an acid catalyst, and
yielding at least a 1,3,5-trimethyl-2,4,6-tris(3,5-tert-butyl-4-hydroxybenzyl)benzene, wherein said process is produced in the absence of a hydrocarbon solvent or a halohydrocarbon solvent.

6. A process comprising:
combining at least acetic acid, paraformaldehyde, a secondary amine, and 2,6-di-tert-butylphenol to yield at least 2,6-di-tert-butyl-4-acetoxyrnethylphenol,
isolating at least the 2,6-di-tert-butyl-4-acetoxymethylphenol as a solid or a melt,
combining at least the 2,6-di-tert-butyl-4-acetoxymethylphenol, mesitylene, and a catalytic amount of an acid catalyst, and
yielding at least a 1,3,5-trimethyl-2,4,6-tris(3,5-tert-butyl-4-hydroxybenzyl)benzene, wherein said process is produced in the absence of a hydrocarbon solvent or a halohydrocarbon solvent.

7. A process comprising:
combining at least acetic acid, paraformaldehyde, a secondary amine, and 2,6-di-tert-butylphenol to yield a solution comprising at least 2,6-di-tert-butyl-4-acetoxymethylphenol,
acidifying the solution,
combining at least the 2,6-di-tert-butyl-4-acetoxymethylphenol, mesitylene, and a catalytic amount of an acid catalyst, and
yielding at least a 1,3,5-trimethyl-2,4,6-tris(3,5-tert-butyl-4-hydroxybenzyl)benzene, wherein said process is produced in the absence of a hydrocarbon solvent or a halohydrocarbon solvent.

8. The process according to claim 1, wherein the secondary amine comprises dimethylamine, diethylamine, methylethylamine, diisopropylamine, methylisoproplyamine, ethylisopropylamine, dipropylamine, methylproplyamine, ethylpropylamine, di-butylamine, methylbutylamine, ethylbutylamine, proplybutylamine, diphenylamine, phenylnaphthylamine, piperidine, or piperazine.

9. The process according to claim 1, wherein the secondary amine comprises dimethylamine or diethylamine.

10. The process according to claim 1, wherein the acid catalyst comprises an alkyl sulfonic acid, an aryl sulfonic acid, chloroacetic acid, trifluoroacetic acid, or sulfuric acid.

11. The process according to claim 1, wherein the acid catalyst comprises sulfuric acid.

12. The process according to claim 1, further comprising recovering unreacted acetic acid.

13. The process according to claim 1, further comprising recovering unreacted acetic acid and repeating the process using the recovered acetic acid.

14. The process according to claim 5, wherein
isolating at least the 2,6-di-tert-butyl-4-acetoxymethylphenol as a solid or a melt, is replaced with
isolating at least the 2,6-di-tert-butyl-4-acetoxymethylphenol as a solid or a melt and purifying the 2,6-di-tert-butyl-4-acetoxymethylphenol.

15. The process according to claim 14, wherein the purifying of the 2,6-di-tert-butyl-4-acetoxymethylphenol comprises washing the 2,6-di-tert-butyl-4-acetoxymethylphenol with water a plurality of times, crystallizing the 2,6-di-tert-butyl-4-acetoxymethylphenol from the acetic acid, precipitating the 2,6-di-tert-butyl-4-acetoxymethylphenol from a hydrocarbon solvent.

16. The process according to claim 14, wherein the purifying of the 2,6-di-tert-butyl-4-acetoxymethylphenol comprises crystallizing the 2,6-di-tert-butyl-4-acetoxymethylphenol from the acetic acid, and further comprising recovering the acetic acid and repeating the process using the recovered acetic acid with new batches of paraformaldehyde, secondary amine, and 2,6-di-tert-butylphenol.

17. The process according to claim 2, further comprising recovering the acetic acid and repeating the process using the recovered acetic acid with new batches of paraformaldehyde, secondary amine, and 2,6-di-tert-butylphenol.

18. A process comprising combining at least acetic acid, paraformaldehyde, a secondary amine, and 2,6-di-tert-butylphenol to yield a solution comprising at least 2,6-di-tert-butyl-4-acetoxyinethylphenol, %, wherein said process is produced in the absence of a hydrocarbon solvent or a halohydrocarbon solvent.

* * * * *